(12) United States Patent
Joshi et al.

(10) Patent No.: US 8,023,709 B2
(45) Date of Patent: Sep. 20, 2011

(54) VASCULATURE PARTITIONING METHODS AND APPARATUS

(75) Inventors: Mukta Chandrashekhar Joshi, Belmont, MA (US); Yogisha Mallya, Karnataka (IN); Srikanth Suryanarayanan, Karnataka (IN); Krishna Seetharam Shriram, Karnataka (IN); Ajay Gopinath, Karnataka (IN)

(73) Assignee: General Electric Company, Schenectady, NY (US)

( * ) Notice: Subject to any disclaimer, the term of this patent is extended or adjusted under 35 U.S.C. 154(b) by 999 days.

(21) Appl. No.: 11/563,115

(22) Filed: Nov. 24, 2006

(65) Prior Publication Data

US 2008/0123800 A1 May 29, 2008

(51) Int. Cl.
*G06K 9/00* (2006.01)

(52) U.S. Cl. ........................................ 382/130; 382/131

(58) Field of Classification Search .................. 382/128, 382/100, 154, 130, 259, 131; 600/433, 481, 600/425

See application file for complete search history.

(56) References Cited

U.S. PATENT DOCUMENTS

| | | |
|---|---|---|
| 2002/0090121 A1* | 7/2002 | Schneider et al. ............ 382/128 |
| 2004/0101179 A1 | 5/2004 | Suryanarayanan et al. |
| 2005/0111732 A1 | 5/2005 | Mallya et al. |
| 2005/0113680 A1* | 5/2005 | Ikeda et al. ................... 600/425 |
| 2006/0036167 A1* | 2/2006 | Shina ............................. 600/433 |
| 2008/0146951 A1* | 6/2008 | Zhao et al. .................... 600/504 |

OTHER PUBLICATIONS

Author: Takemura et al.; Title: Automatic segmentation method which divides a cerebral artery tree in Time-Of-Flight MR-Angiography into artery segments.; Item: Medical Imaging 2006: Image Processing; Date: 2006; pp. 9; vol. 6144, 61443G.

* cited by examiner

*Primary Examiner* — Vu Le
*Assistant Examiner* — Claire X Wang
(74) *Attorney, Agent, or Firm* — ZPS Group, SC

(57) ABSTRACT

A method includes performing an automatic partitioning of Neuro-vessels into a plurality of anatomically relevant circulatory systems using a CT system.

17 Claims, 6 Drawing Sheets

Multi object volume rendering of the major circulatory systems.

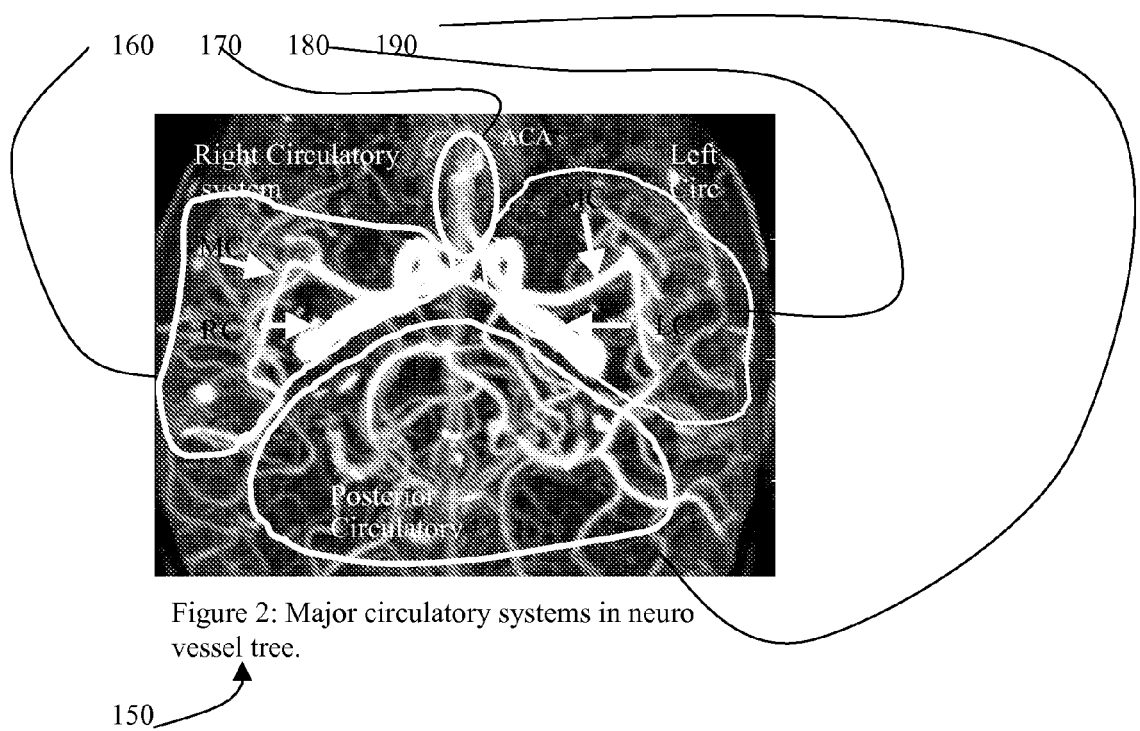
Figure 2: Major circulatory systems in neuro vessel tree.

Figure 3 Circle of Willis
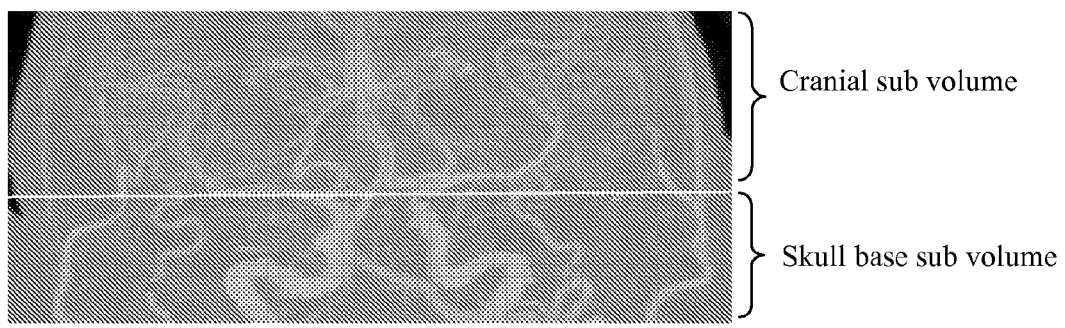
Figure 4: MIP rendering of the bone free CTA volume with partition line that divides the entire volume in to cranial and skull base sub volume.

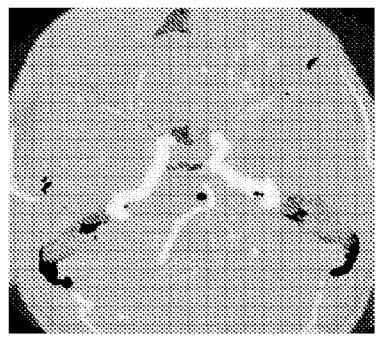
Figure 5: Axial MIP (projection image) of the skull base volume. The internal carotid arteries form left and right bounds of the posterior circulatory system.
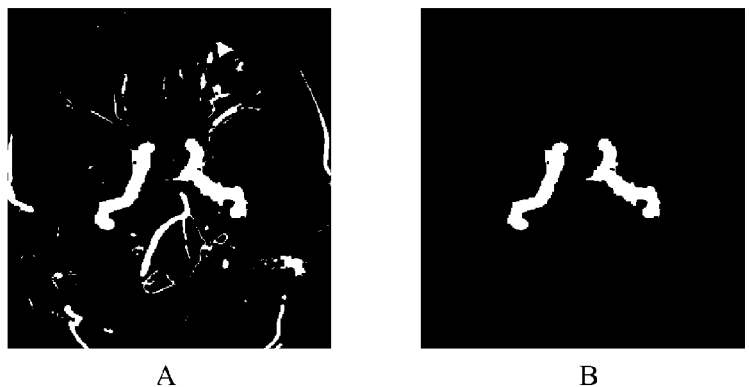
A          B
Figure 6: (A) Threshold of 150HU is applied on the projection image. (B) Extracted right and left internal carotid based on their relative size and locations in the projection image.

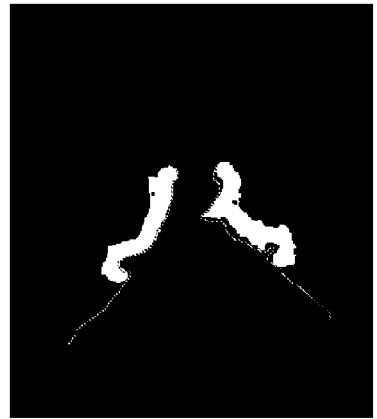

Figure 7: Two Piecewise lines are generated by detecting the boundaries of the internal carotid arteries. The piecewise lines demarcate posterior circulatory system from left/right circulatory system.

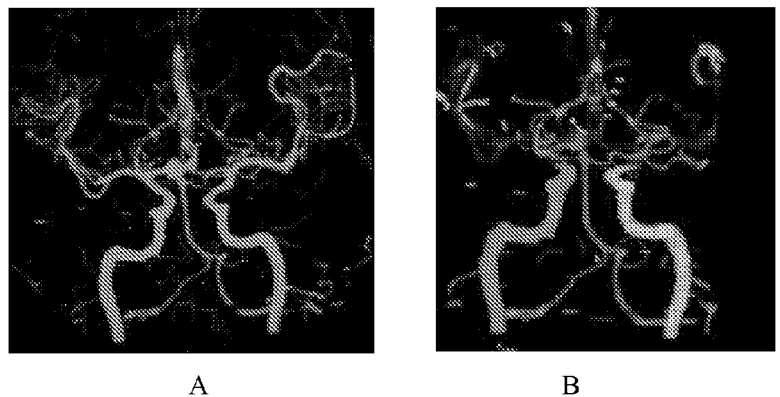

A                    B

Figure 8: (A) Neuro vessel tree extracted from CTA volume. (B) In the first step, posterior circulatory system in the entire volume and right/left internal carotids in the skull base region are labeled.

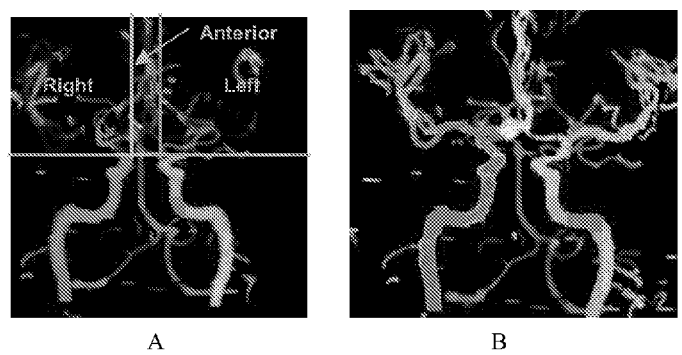
Figure 9: (A) Expanse of the right/left carotid arteries in the skull base volume is extended to cranial sub volume. (B) The expanse divides the cranial sub volume in to right, left and anterior circulatory system.
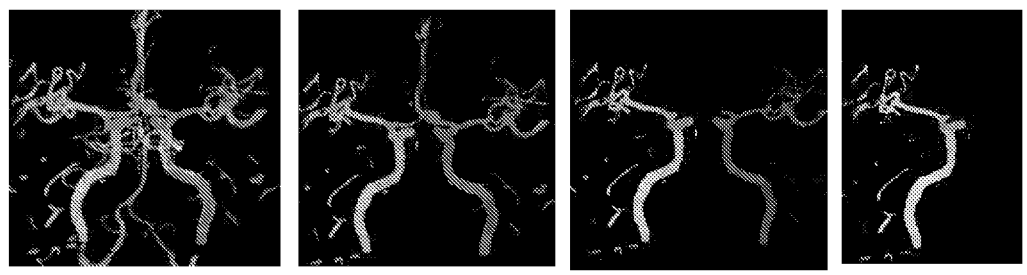
Figure 10: Multi object volume rendering of the major circulatory systems.

VASCULATURE PARTITIONING METHODS AND APPARATUS

BACKGROUND OF THE INVENTION

This invention relates generally to imaging methods and apparatus, and more particularly, to methods and apparatus that provide for vasculature partitioning.

Computed Tomography Angiography (CTA) and Magnetic Resonance Angiography (MRA) protocols for Neuro-imaging are done during stroke workup to identify vascular root causes for the stroke. The review of CTA and MRA datasets sometimes can be difficult due to any bone obstructions, and/or any clutter from any overlapping of Neuro-vessels in a three dimensional (3D) visualization.

Clinically there is a need to be able to generate views that can offer a clear picture in a 3D visualization of the Neuro-vasculature that can allow radiologists to rule out aneurysms. One way to solve that need is to create views that remove the bone obstruction and reduce the clutter through anatomically relevant division of the Neuro-vascular volume. Therefore it would be desirable to have a workflow that provides for the efficient and timely review of CTA (and MRA) data by automatically generating 3D views rendered in maximum intensity projection (MIP) views and automatically perform a volume rendering of the Neuro-vasculature to automatically anatomically divide the vasculature into left, right, anterior, and posterior circulatory regions, in one embodiment.

BRIEF DESCRIPTION OF THE INVENTION

In one aspect, a method includes performing an automatic partitioning of Neuro-vessels into a plurality of anatomically relevant circulatory systems using a CT system.

In another aspect, a computer readable medium is embedded with a program configured to instruct a computer to automatically partition Neuro-vessels into anatomically relevant circulatory systems, and automatically label each partitioned system.

In yet another aspect, a system includes an x-ray source, an x-ray detector positioned to receive x-rays emitted from the source, and a computer configured to receive data from the detector either directly or remotely over a network or otherwise. The computer is configured to automatically partition Neuro-vessels into anatomically relevant circulatory systems, and fuse the partitioned systems with at least one region of interest.

In yet still another aspect, a system includes an x-ray source, an x-ray detector positioned to receive x-rays emitted from the source, and a computer configured to receive data from the detector either directly or remotely over a network or otherwise. The computer is configured to automatically partition vasculature into anatomically relevant circulatory systems, automatically analyze specific sub branches of the vasculature, automatically detect and measure any vascular abnormalities, and automatically generate specific views of the anatomy and any pathology.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 illustrates a plurality of circulatory systems.
FIG. 3 illustrates a Circle of Willis.
FIG. 4 illustrates a MIP rendering.
FIG. 5 illustrates an axial MIP rendering of the skull base.
FIG. 6 illustrates thresholding and extracting.
FIG. 7 illustrates piecewise lines.
FIG. 8 illustrates Neuro-or neuro vessels extracted from a volume and its labeled posterior circulatory system, left and right circulatory system in the skull base.
FIG. 9 illustrates dividing the cranial sub volume in to the right, left, and anterior circulatory systems.
FIG. 10 illustrates Multi-object volume rendering of the major circulatory systems.

DETAILED DESCRIPTION OF THE INVENTION

Figure 1:
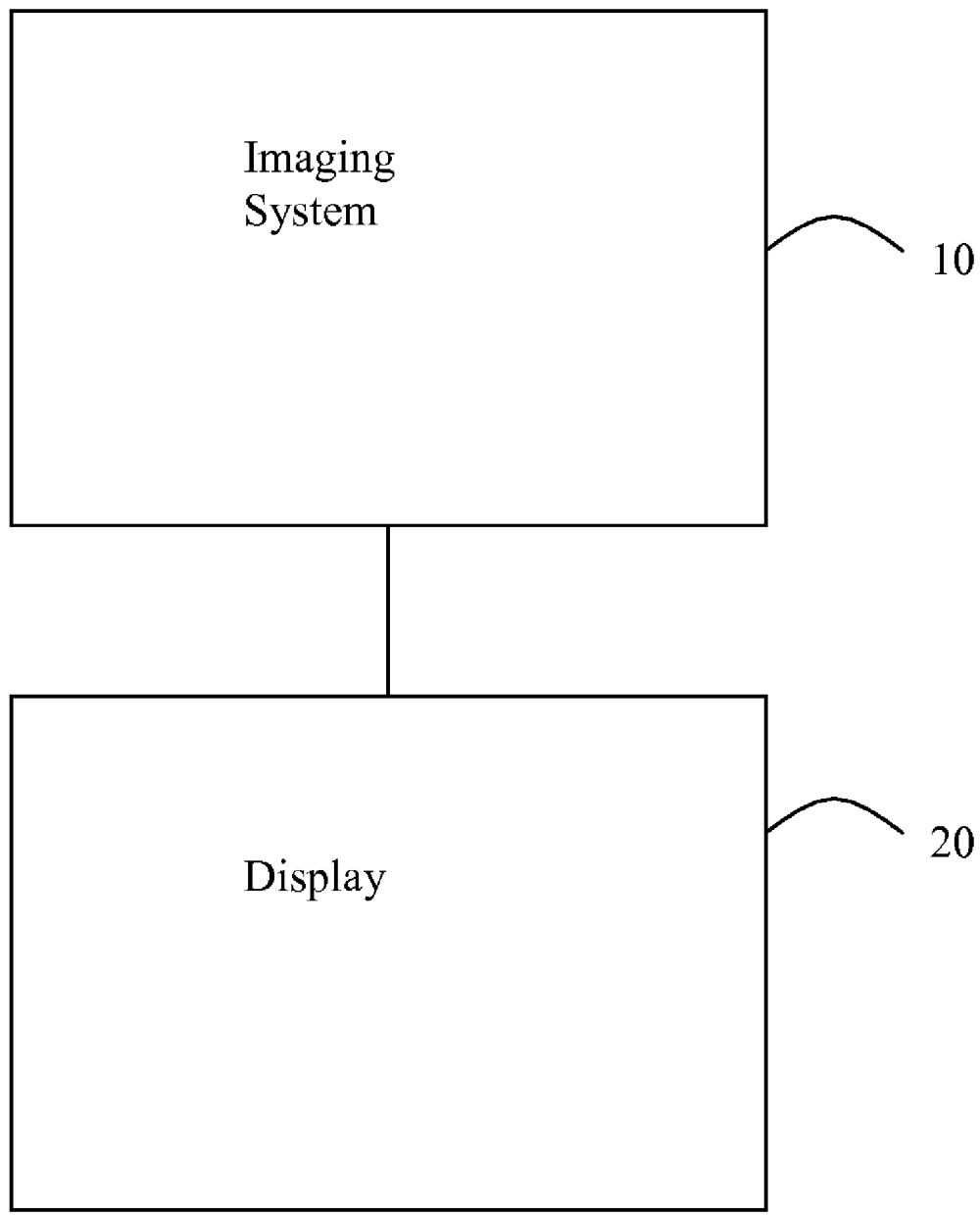
FIG. 1 illustrates an exemplary diagnostic imaging system.

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray system, it is contemplated that the benefits of the invention accrue to all diagnostic imaging systems and modalities such as PET, MRI, SPECT, Ultrasound, fused systems such as a CT/PET system, and/or any modality yet to be developed in which partitioning of Neuro-vessels into a plurality of anatomically relevant circulatory systems is desirable.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and the below described obtainment/attainment of a non-scanner dependent patient specific metric can be done in one modality (e.g., CT) and the processed data can be transferred to the other modality (e.g., PET). Display 20 can be separate from system 10 or integrated with system 10. System 10 includes an acquisition device such as an x-ray radiation detector, a Gamma Camera, an ultrasound probe and/or an MRI coil.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid state image detector, for example, although conventional film images stored in digital form in the memory may also be processed. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

The herein described methods and apparatus provide for an automatic partitioning of Neuro-vessel tree into anatomically relevant circulatory systems as shown in the FIG. 2. FIG. 2 illustrates a partitioning of the Neuro-vasculature into a plurality 150 of circulatory systems including a right circulatory system 160, an anterior circulatory system 170, a left circulatory system 180, and a posterior circulatory system 190. The partitioning may be performed at a computer that is part of an imaging system or at a computer remote from the system, such as, for example, a 3D workstation.

The separation of a Neuro-vessel tree into posterior and left/right carotid system is challenging due to the "Circle of Willis" (COW), which is a closed loop formed by the arteries, in the cranial region as shown in the FIG. 3. The circle consists of the anterior communicating arteries (ACOM) that connect the L/R circulation and the posterior communicating arteries (PCOM) that connect the anterior/posterior circulation. Ideally, one would simply "detach" the communicating arteries to derive separate unconnected circulation components. In a small set of cases, it was observed that the posterior communicating arteries are small and non-viable (insufficient contrast due to small vessel size and therefore non-visible). In these situations, the posterior circulation system is cleanly separated from the other vessels using a 3-D connectivity test. However, in the majority of cases, the PCOMS are viable and the difficulty arises in modeling and identifying the circle due to a large number of "normal" anatomical variations in its topology. To overcome this challenge, one can follow the path of the carotid arteries to identify cut planes useful to separate the circulation components (systems). The entire head may be divided into two sub volumes, cranial sub volume, and skull base sub volume, as shown in FIG. 4. In one embodiment, the division of the head into cranial and skull base sub volume is achieved as taught by US patent application US20040101179 (A1).

Partitioning of the vessel tree may be achieved first in the skull base sub volume and then the results are propagated to the cranial sub volume. An axial Maximum Intensity Projection (MIP) of the vessels in the skull base sub-volume is created as shown in the FIG. 5. It is apparent in the axial projection image that the internal carotid arteries form left and right bounds for the posterior circulatory system. The right and left internal carotid arteries (ICA) are extracted based on their relative size and positions in the projection image as shown in the FIG. 6. In FIG. 6 part A, first a thresholding is done where the high opacity structure is isolated by choosing a threshold value of between 110 and 175 Hounsfield units (HU). Empirically and by looking at FIG. 6, 150 HU is a good lower threshold. The threshold value can be obtained automatically by analyzing the intensity distribution of the axial projection images. Once the thresholding is done, the two largest structures in the image are the arteries and can be easily isolated in part B.

Referring now to FIG. 7, a piecewise line fitting approach has been implemented for automatic division of Neuro-vasculature in to right, left, posterior, and anterior circulatory system. The algorithm starts with a segmented vessel volume of CT Angiography (CTA). An Auto Bone algorithm developed earlier automatically strips the bone and creates a vessel only volume. A piecewise line is generated per ICA from the their boundary points as shown in the FIG. 7. The piecewise lines hence generated separate posterior circulatory system from the left/right circulatory system in the cranial and skull base volume as shown in FIG. 8. The expanse of the left and right carotids in the skull base region is extended to cranial region as shown in the FIG. 9 to separate anterior cerebral artery (ACA) from left and right middle cerebral arteries (MCA).

The herein described methods and apparatus provide for an improved visualization. The herein described methods and apparatus will allow multi object rendering of the Neuro-vessel tree. The user can fade-in or fade-out circulatory system of interest in the vasculature as demonstrated in the FIG. 10. For example, in the left side of FIG. 10, a user can see the left, right, posterior, and anterior circulatory systems. While moving one slide over, the posterior system is removed. In addition, moving to the right, the anterior system is removed, and, in the last slide, only the right circulatory system is shown. This so-called Fade-In/Fade-out CT mode allows for the clutter free visualization of Neuro-vasculature.

The herein described methods and apparatus also provide for "Ready to Read" workflow. Ready to Read workflow means, in one embodiment, the automatic extraction of vasculature, analyzing specific sub branches, detection/measurement of vascular abnormalities and generating custom specific views of the pathology and the anatomy, are all provided. In other words, there is a general vasculature structure that is common to most people, but the pathology can be anywhere and any size, and based on the size and orientation of the pathology, a view specific to the pathology is generated.

In one embodiment, the labeling of the major circulatory components in the 3D Neuro-vessel tree is achieved using axial and coronal projection image (thus it is done in a two dimensional (2D) environment). Hence, the computation time is significantly less than performing the labeling in the 3D dataset.

The herein described methods and apparatus allow for easy scalability, in that the herein described methods and apparatus can be easily extended to other modalities like MR (MRA, TOF cases etc) for example.

The herein described methods and apparatus do not require any explicit models of the vessel tree. Explicit modeling of the Neuro-vasculature can be difficult due to high variability of the Neuro-anatomy, resulting in poor segmentation accuracy.

The labeled tree in the cerebral sub volume can be used to automatically to label the brain in to right MCA, left MCA, ACA, and posterior territory. This labeling is useful to predict which parts of the brain will be impacted (hence the function) due to reduced or ceased blood flow from a specific circulatory component(s). Of course, the labeling can be more customized and then instead of labeling the right middle cerebral artery "right MCA", additional vascular structures on the right side could be included with the right MCA and then that area be labeled "RCS" for right circulatory system. Of course, other labeling may be done as well.

Labeled vessel tree can be used to construct an atlas of the Neuro-vessel tree. The template hence created can be used for segmentation and labeling of the Neuro-vasculature in a new case.

The herein described methods and apparatus provide for better visualization in surgical planning systems, which is one technical effect. For example, in one embodiment, a fusion of the labeled tree with a region of interest such as a tumor (or a stroke site, a potential tumor and/or a potential stroke site) can be used to improve the planning of surgical procedure in Neuro-anatomy. For example: a Spoiled Gradient Recalled sequence (SPGR) provides high-resolution anatomical details of structures such as the brain, a tumor etc. and the time of flight (TOF) data provides 3D vessel structure. Fusion of the labeled tree with SPGR data, and with a region of interest such as a tumor in SPGR would provide valuable information like which circulatory systems feed the tumor or brain regions that will be effected due to accidental removal of a vessel etc. Fusion of the labeled tree with a region of interest being a suspected or potential stroke site should be beneficial.

Technical effects include better visualization of vasculature of the human body or other animal as well. "Ready to Read" is another technical effect.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising:
   performing an automatic partitioning of Neuro-vessels into a plurality of anatomically relevant circulatory systems using a CT system, wherein each of the plurality of anatomically relevant circulatory systems comprises a specific sub-branch of Neuro-vessels;
   automatically labeling each circulatory system;
   fusing the labeled circulatory systems in a visualization with at least one separate image, wherein the at least one separate image represents at least one region of interest; and
   displaying a number of anatomically relevant circulatory systems on a display, wherein the number displayed is greater than one and fewer than all anatomically relevant circulatory systems.

2. The method in accordance with claim 1 wherein said automatically labeling further comprises automatically labeling each circulatory system in a 2D environment.

3. The method in accordance with claim 1 wherein the region of interest includes at least one of a stroke location and a tumor.

4. The method in accordance with claim 1 further comprising automatically analyzing specific sub branches of the vessels.

5. The method in accordance with claim 4 wherein automatically analyzing specific sub branches of the vessels comprises at least one of detecting and measuring vascular abnormalities.

6. A non-transitory computer readable medium having a computer program stored thereon, the computer program configured to instruct a computer to:
   automatically partition Neuro-vessels into a plurality of anatomically relevant circulatory systems;
   automatically label each partitioned circulatory system;
   fuse one or more partitioned circulatory systems with another image representing at least one region of interest; and
   display a number of anatomically relevant circulatory systems on a display, wherein the number displayed is greater than one and fewer than all anatomically relevant circulatory systems.

7. The non-transitory computer readable medium in accordance with claim 6 wherein said computer is further configured to automatically label each partitioned circulatory system in a 2D environment.

8. A system comprising:
   an x-ray source;
   an x-ray detector positioned to receive x-rays emitted from said source; and
   a computer configured to receive data from said detector either directly or remotely over a network or otherwise, said computer configured to:
      automatically partition Neuro-vessels into a plurality of anatomically relevant circulatory systems;
      automatically label the partitioned circulatory systems;
      fuse the partitioned circulatory systems with another image representing at least one region of interest; and
      display the fused partitioned circulatory systems and the another image on a display, wherein the computer is further configured to fade-in or fade-out on a specific view of the partitioned circulatory systems based on a user selection of the specific view.

9. The system in accordance with claim 8 wherein said region of interest comprises a potential tumor.

10. The system in accordance with claim 8 wherein said region of interest comprises a potential stroke site.

11. The system in accordance with claim 8 wherein said computer is further configured to automatically label each circulatory system in a 2D environment.

12. The system in accordance with claim 11 wherein said computer is further configured to perform the automatic partitioning without having an explicit model of the vessels available.

13. The system in accordance with claim 8 wherein said computer is further configured to fuse the labeled circulatory systems in a visualization with the at least one region of interest wherein the region of interest includes at least one of a potential stroke location and potential tumor.

14. The system in accordance with claim 13 wherein said computer further configured to automatically analyze specific sub branches of the Neuro-vessels.

15. The system in accordance with claim 14 wherein said computer is further configured to detect and measure vascular abnormalities.

16. A system comprising:
   an x-ray source;
   an x-ray detector positioned to receive x-rays emitted from said source; and
   a computer configured to receive data from the detector either directly or remotely over a network or otherwise, said computer configured to:
      automatically partition vasculature into a plurality of anatomically relevant circulatory systems;

automatically analyze specific sub branches of the vasculature;

automatically detect and measure vascular abnormalities;

automatically generate specific views of the specific sub branches of the vasculature, wherein each of the specific sub branches of the vasculature are rendered in a different color;

automatically fuse at least one specific view of a specific sub branch with another image representing at least one region of interest; and display at least one of the fused specific views.

17. The system of claim 16 wherein the plurality of anatomically relevant circulatory systems comprise left, right, anterior, and posterior circulatory regions.

* * * * *